United States Patent
Nishizaki

(10) Patent No.: US 10,251,897 B2
(45) Date of Patent: Apr. 9, 2019

(54) GLUT4 ENDOCYTOSIS INHIBITOR

(71) Applicant: NISHIZAKI BIOINFORMATION RESEARCH INSTITUTE, Kobe-shi, Hyogo (JP)

(72) Inventor: Tomoyuki Nishizaki, Kobe (JP)

(73) Assignee: NISHIZAKI BIOINFORMATION RESEARCH INSTITUTE, Kobe (JP)

( * ) Notice: Subject to any disclaimer, the term of this patent is extended or adjusted under 35 U.S.C. 154(b) by 0 days.

(21) Appl. No.: 15/111,545

(22) PCT Filed: Jan. 16, 2015

(86) PCT No.: PCT/JP2015/051022
§ 371 (c)(1),
(2) Date: Jul. 14, 2016

(87) PCT Pub. No.: WO2015/108134
PCT Pub. Date: Jul. 23, 2015

(65) Prior Publication Data
US 2016/0331769 A1 Nov. 17, 2016

(30) Foreign Application Priority Data

Jan. 17, 2014 (JP) ................................. 2014-007232

(51) Int. Cl.
*A61K 31/685* (2006.01)
(52) U.S. Cl.
CPC .................... *A61K 31/685* (2013.01)
(58) Field of Classification Search
CPC .................................................. A61K 31/685
See application file for complete search history.

(56) References Cited

U.S. PATENT DOCUMENTS

| 5,681,747 | A | 10/1997 | Boggs et al. |
| 6,015,892 | A | 1/2000 | Bennett et al. |
| 9,028,863 | B2 | 5/2015 | Kester et al. |
| 9,326,953 | B2 | 5/2016 | Kester et al. |
| 2004/0009216 | A1 | 1/2004 | Rodrigueza et al. |
| 2004/0067910 | A1 | 4/2004 | Msika et al. |
| 2005/0025820 | A1 | 2/2005 | Kester et al. |
| 2008/0213351 | A1 | 9/2008 | Rodrigueza et al. |
| 2008/0221017 | A1 | 9/2008 | Msika et al. |
| 2011/0009333 | A1 | 1/2011 | Msika et al. |

(Continued)

FOREIGN PATENT DOCUMENTS

| CL | 2309614 C1 | 11/2007 |
| JP | H08-507929 A | 8/1996 |

(Continued)

OTHER PUBLICATIONS

STN compound data, accessed Mar. 1, 2017.*

(Continued)

*Primary Examiner* — Angela C Brown-Pettigrew
(74) *Attorney, Agent, or Firm* — Leydig, Voit & Mayer, Ltd.

(57) ABSTRACT

The present invention provides a therapeutic drug for diabetes containing 1,2-dioleoyl-sn-glycerol-3-phosphoethanolamine (DOPE) as an active ingredient, particularly a therapeutic drug for diabetes that exhibits a GLUT4 endocytosis suppressive action by suppressing activation of PKCα and the like.

6 Claims, 3 Drawing Sheets

Specification includes a Sequence Listing.

(56) References Cited

U.S. PATENT DOCUMENTS

| | | | |
|---|---|---|---|
| 2012/0100077 A1* | 4/2012 | Hoffmann | C12N 1/06 424/9.6 |
| 2013/0295159 A1 | 11/2013 | Kester et al. | |

FOREIGN PATENT DOCUMENTS

| | | | |
|---|---|---|---|
| JP | 2004-513919 A | 5/2004 | |
| JP | 2005-247728 A | 9/2005 | |
| JP | 2005-527582 A | 9/2005 | |
| JP | 2006-524707 A | 11/2006 | |
| WO | WO 2009/028220 A1 | 3/2009 | |

OTHER PUBLICATIONS

Ilarduya et al (Biochimica et Biophysica Acta 1561 (2002) 209-221).*
Konstantopoulos N., Molero-Navajas J.C. ((2009) The Measurement of GLUT4 Translocation in 3T3-L1 Adipocytes. In: Stocker C. (eds) Type 2 Diabetes. Methods in Molecular Biology (Methods and Protocols), vol. 560. Humana Press).*
Ferrarri et al (Nucleic Acids Research, 2001, vol. 29, No. 7).*
Ma et al (Journal of Endocrinology (2013) 216, 353-362).*
Tana et al., Journal of Veterinary Medical Science, 59(7): 617-619 (1997).
Tsuchiya et al., Life Sciences, 93(5-6): 240-246 (2013).
Yaguchi et al., Behavioural Brain Research, 204: 129-132 (2009).
Yaguchi et al., Life Sciences, 84: 263-266 (2009).
Japan Patent Office, International Search Report in International Patent Application PCT/JP2015/051022 (dated Apr. 21, 2015).
Leto et al., *Nat. Rev. Mol. Cell Biol.*, 13(6): 383-396 (2012).
Park et al., *Int. J. Pharm.*, 415(1-2): 267-272 (2011).
European Patent Office, Extended European Search Report in European Patent Application No. 15737584.1 (dated Jul. 3, 2017).

* cited by examiner

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 1
gaacgugcau gaggugaaat t                    21

<210> SEQ ID NO 2
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 2
uuucaccuca ugcacguuct t                    21

GLUT4 ENDOCYTOSIS INHIBITOR

CROSS-REFERENCE TO RELATED APPLICATIONS

This patent application is the U.S. national phase of International Patent Application No. PCT/JP2015/051022, filed on Jan. 16, 2015, which claims the benefit of Japanese Patent Application No. 2014-007232, filed Jan. 17, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 608 bytes ASCII (Text) file named "726989SequenceListing.txt," created Jul. 13, 2016.

TECHNICAL FIELD

The present invention relates to a phospholipid compound having a diabetes treatment effect, more specifically, a therapeutic drug for diabetes containing 1,2-dioleoyl-sn-glycerol-3-phosphoethanolamine (DOPE) as an active ingredient and the like.

BACKGROUND ART

Diabetes is a disease in which the function of insulin becomes insufficient, the blood glucose level becomes high, and sugar is detected even in urine. Insulin is produced in and secreted from pancreatic β cells, promotes synthesis of glycogen (storage type glucose) from glucose in the liver and muscle, suppresses degradation of glycogen into glucose in the liver, and suppresses increase in the blood glucose level.

The number of patients is increasing mainly due to overeating, lack of exercise, obesity, stress, and genetic factors.

Diabetes is largely divided into type 1 diabetes showing absolute lack of insulin, and type 2 diabetes showing relative lack of insulin. Type 1 is basically treated with insulin injection, and type 2 is basically treated with diet and exercise therapy, though drug therapy is necessary when the blood glucose cannot be controlled well. For drug therapy, oral therapeutic drug for diabetes or insulin is used, both of which require improvement in terms of side effects, QOL and the like.

In addition, the condition developing lifestyle-related diseases such as hypertension, hyperlipidemia, diabetes and the like due to the accumulated visceral fat is referred to as metabolic syndrome, and has been widely recognized to increase the risk of developing arteriosclerotic diseases (myocardial infarction, cerebral infarction etc.). Accordingly, the prophylaxis or treatment of diabetes is necessarily effective for the prophylaxis or treatment of metabolic syndrome.

Phospholipid has various biological activities and, for example, a certain kind of phospholipid has been reported to be effective for the improvement of cognitive function and neurodegenerative disease. For example, 1,2-dilinoleoyl-sn-glycero-3-phosphocholine and 1-palmitoyl-2-oleoyl-sn-glycero-3-phosphocholine have been reported to improve spatial learning disorder and memory disorder induced by scopolamine, or mild cognitive impairment and dementia (non-patent documents 1, 2).

Also, phosphatidylethanolamine is a phospholipid, which is one of the main components of biological membrane, and is being marketed along with phosphatidylserine and the like as health foods. Of phosphatidylethanolamines, particularly, dilinoleoyl phosphatidylethanolamine (containing two linoleic acids as fatty acids) has been reported to have cell death induction suppressive activity, particularly, endoplasmic reticulum stress suppressive activity and, due to such activity, dilinoleoyl phosphatidylethanolamine can be used for pharmaceutical application, particularly for the prophylaxis and/or treatment of neurodegenerative disease (patent document 1).

In addition, phospholipid used for biological membrane model, liposome preparation and the like has also, been reported.

DOCUMENT LIST

Patent Document

Patent document 1: JP-A-2005-247728

Non-Patent Documents

Non-patent document 1: Yaguchi T, Nagata T, Nishizaki T. Dilinoleoylphosphatidylcholine ameliorates scopolamine-induced impairment of spatial learning and memory by targeting alpha-7 nicotinic ACh receptors. Life Sci 2009; 84:263-6 non-patent document 2: Yaguchi T, Nagata T, Nishizaki T. 1-Palmitoyl-2-oleoyl-sn-glycero-3-phosphocholine improves cognitive decline by enhancing long-term depression. Behav Brain Res 2009; 204:129-32

SUMMARY OF THE INVENTION

Problems to be Solved by the Invention

The present invention aims to find a compound having a novel action mechanism in the diabetes treatment effect and provide a pharmaceutical use of the compound.

Means of Solving the Problems

The present inventor has conducted intensive studies in view of the aforementioned problems and found that 1,2-dioleoyl-sn-glycerol-3-phosphoethanolamine (DOPE) has a superior pharmacological action useful for the treatment of diabetes, which resulted in the completion of the present invention. Accordingly, the present invention is as described below.

[1] A GLUT4 (glucose transporter 4) endocytosis inhibitor comprising DOPE as an active ingredient.
[2] The inhibitor of [1], wherein suppression of GLUT4 endocytosis is caused by suppression of PKCα activation.
[3] A PKCα activation inhibitor comprising DOPE as an active ingredient.
[4] A therapeutic drug for diabetes comprising the inhibitor of any of the above-mentioned [1]-[3].
[5] A therapeutic drug for diabetes comprising DOPE as an active ingredient.
[6] The therapeutic drug of the above-mentioned [4] or [5], wherein diabetes is type 2 diabetes.

[7] A therapeutic drug for metabolic syndrome comprising DOPE as an active ingredient.
[8] The inhibitor of any of the above-mentioned [1]- [3], which is a reagent for study.
[9] A treatment method of diabetes, comprising administering an effective amount of DOPE to a subject in need thereof.
[10] The method of the above-mentioned [9], wherein diabetes is type 2 diabetes.
[11] The method of the above-mentioned [9], comprising suppressing GLUT4 endocytosis.
[12] The method of the above-mentioned [11], wherein suppression of GLUT4 endocytosis is caused by suppressing PKCα activation.
[13] DOPE for use for the treatment of diabetes.
[14] DOPE of the above-mentioned [13], wherein diabetes is type 2 diabetes.
[15] DOPE of the above-mentioned [13], which suppresses GLUT4 endocytosis.
[16] DOPE of the above-mentioned [15], wherein suppression of GLUT4 endocytosis is caused by suppressing PKCα activation.
[17] A method of suppressing GLUT4 endocytosis, comprising treating a cell with DOPE.
[18] The method of the above-mentioned [17], wherein suppression of GLUT4 endocytosis is caused by suppressing PKCα activation.
[19] A method of treating metabolic syndrome, comprising administering an effective amount of DOPE to a subject in need thereof.

Effect of the Invention

DOPE has a pharmacological action superior for the treatment of diabetes (protein kinase Cα (PKCα) activation suppressive action, glucose transporter 4 (GLUT4) endocytosis suppressive action and blood glucose level-lowering action), and therefore, is useful as a therapeutic drug for diabetes. It is also useful as various reagents based on such pharmacological action.

Figure 1:
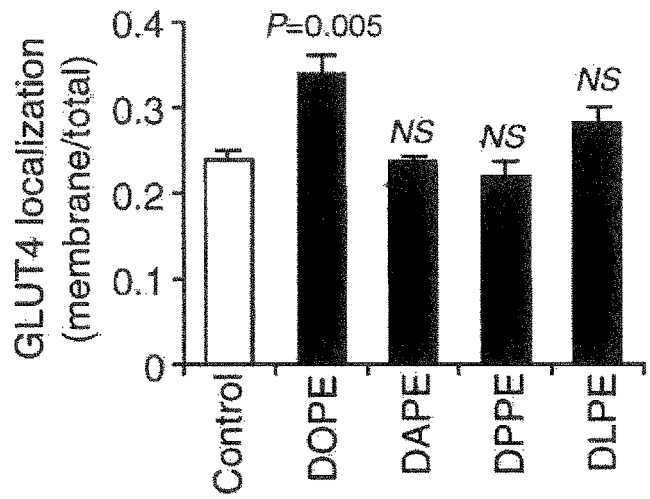
FIG. 1 is a graph showing that DOPE has an action to increase cellular membrane distribution of GLUT4 in differentiated 3T3L1-GLUT4myc adipocytes. The cells were not treated with (Control), or treated with 1 μM of various phospholipid derivatives and, after 20 min, lysed, and separated into the cytoplasm (C) fraction and cellular membrane (M) fraction, after which Western blotting was performed using an anti-c-myc antibody. In the graph, each column shows mean (±SD) of the ratio: (signal intensity of c-myc in cellular membrane fraction)/(signal intensity of c-myc in in total cells) (n=4 in each experiment). P value, ANOVA (Bonferroni adjustment). NS; not significant. DOPE; 1,2-dioleoyl-sn-glycero-3-phosphoethanolamine, DAPE; 1,2-diarachidonoyl-sn-glycero-3-phosphoethanolamine, DPPE; 1,2-dipalmitoleoyl-sn-glycero-3-phosphoethanolamine, DLPE; 1,2-dilinoleoyl-sn-glycero-3-phosphoethanolamine.

DESCRIPTION OF EMBODIMENT 1,2-Dioleoyl-sn-glycerol-3-phosphoethanolamine used as an active ingredient in the present invention (abbreviated as DOPE as necessary in the present specification) has the following structural formula. It is known that DOPE can be used as a biological membrane model and for the preparation of liposomes; however, DOPE is not reported to have a particular efficacy in itself.

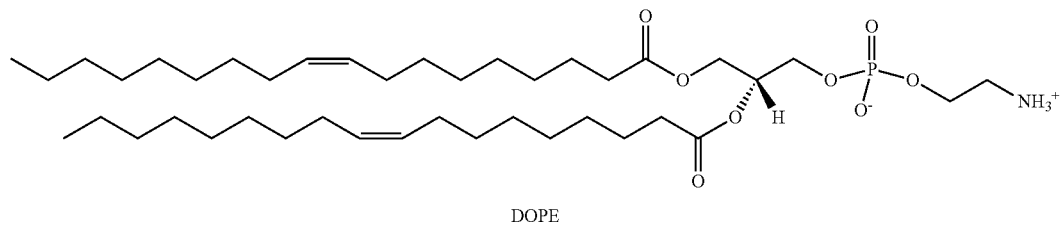 [SMILES: CCCCCCCC/C=C\CCCCCCCC(=O)OC[C@H](COP(=O)([O-])OCC[NH3+])OC(=O)CCCCCCC/C=C\CCCCCCCC]

DOPE

DOPE can be produced by a method known per se. While DOPE has optical isomers, such isomers and mixtures thereof are all encompassed in the scope of the present invention. DOPE is also commercially available and marketed from, for example, Avanti Polar Lipids (Alabaster, Ala., USA).

The DOPE in the present invention may also be used in the form of a salt thereof. Such salt is not particularly limited, and a salt acceptable as a medicine or food is preferable. Examples thereof include salts with inorganic base (e.g., alkali metal such as sodium, potassium and the like; alkaline earth metal such as calcium, magnesium and the like; aluminum, ammonium), organic base (e.g., trimethylamine, triethylamine, pyridine, picoline, ethanolamine, diethanolamine, triethanolamine, dicyclohexylamine, N,N-dibenzylethylenediamine), inorganic acid (e.g., hydrochloric acid, hydrobromic acid, nitric acid, sulfuric acid, phosphoric acid), organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), basic amino acid (e.g., arginine, lysine, ornithine) or acidic amino acid (e.g., aspartic acid, glutamic acid) and the like.

When used in the present specification, the test subject can be a mammal. Examples of such mammal include primates (e.g., human, monkey, chimpanzee), rodents (e.g., mouse, rat, guinea pig), pets (e.g., dog, cat, rabbit), working animals and domestic animals (e.g., bovine, horse, swine, sheep, goat), with preference given to human.

DOPE has, as shown by the data in the Examples, (1) PKCα activation suppressive action, (2) suppressive action on GLUT4 endocytosis, and (3) blood glucose level-lowering action.

(1) PKCα Activation Suppressive Action

PKC was identified as one of the maximum gene family of non-receptor serine-threonine protein kinase (Kikkawa et al., J. Biol. Chem., 257, 13341 (1982)). Many physiological signaling mechanisms are considered to be caused by this enzyme. The PKC gene family is currently constituted of genes classified into 4 subgrounds: 1) classical PKCα, $β_1$, $β_2$ and γ, 2) novel PKCδ, ε, η and θ, 3) atypical PKCζ, λ, η and ι, and 4) PKCμ. PKCα is constituted of two C1 domains (C1a, C1b) and C2 domain and catalytic domain. It has been reported that PKCα shows a behavior completely different from that of other PKC in cancer and the like, and is a signal extremely important for oncogenesis. Therefore, a PKCα activation inhibitor may be usable as an anti-cancer agent.

Moreover, the present invention has clarified that suppression of PKCα activation induces a suppressive action on GLUT4 endocytosis. Therefore, a PKCα activation inhibitor may be usable as a therapeutic drug for diabetes.

(2) Suppressive Action on GLUT4 Endocytosis

GLUT4 expressed in adipocytes and skeletal muscle cells is hardly exposed on the cellular membrane in the absence of insulin stimulation, and exists in the state of being incorporated in an intracellular vesicle group. Insulin stimulation promotes transport of GLUT4 present in the intracellular vesicle onto a cellular membrane to increase the amount of GLUT4 that appears on the surface of cellular membrane, and uptake glucose into the cells to lower the blood glucose level. While promotion of sugar uptake induced by insulin is physiologically important, the physiological phenomenon in the case of diabetes is known to be disordered remarkably. In the absence of stimulation of insulin, GLUT4 internally transfers again into intracellular vesicle group from cellular membrane (endocytosis).

When β cells in the pancreas die for some reason, insulin secretion is disordered and diabetes is developed (type 1 diabetes). At present, the sole treatment of type 1 diabetes is insulin injection from outside the body. On the other hand, marked attenuation of sugar uptake in response to insulin stimulation (insulin resistance=attenuation of insulin response) also triggers the onset of diabetes (type 2 diabetes). For the treatment of type 2 diabetes, insulin secretion stimulant, intestinal sugar absorption inhibitor, disaccharide decomposition inhibitor, DPP-4 inhibitor, PPARγ activator and the like have been used.

Since intracellular sugar uptake occurs via GLUT4 on the cellular membrane, a medicament that increases distribution of GLUT4 on the cellular membrane, or has an action to suppress a decrease thereof enables promotion of intracellular sugar uptake, and is expected to show its effect as a therapeutic drug for diabetes, irrespective of type 1 or type 2 diabetes.

As used herein, the "cell" is not particularly limited as long as it is capable of glucose uptake, and adipocyte, skeletal muscle cell, hepatocyte and the like can be mentioned.

(3) Blood Glucose Level-lowering Action

Since DOPE can lower the blood glucose level without using insulin, it is useful for the treatment of type 2 diabetes.

By these superior pharmacological actions, the present invention is useful as a prophylactic and/or therapeutic drug for diabetes, as well as a prophylactic and/or therapeutic drug for metabolic syndrome (hereinafter to be also referred to as the medicine of the present invention). As used in the present specification, "prophylaxis" means prevention of exteriorization of symptoms in test subjects free from such symptoms, and the "treatment" means mitigation of symptoms, prevention or delay of exacerbation of symptoms in test subjects showing such symptoms.

Due to such pharmacological actions of DOPE, the present invention can provide a method of suppressing PKCα activation, a method of suppressing GLUT4 endocytosis, a method for the prophylaxis and/or treatment of diabetes, and a method for the prophylaxis and/or treatment of metabolic syndrome (hereinafter to be also simply referred to as the method of the present invention).

When used in the present specification, the cell to be the target of processing with DOPE is not particularly limited as long as it can express. GLUT4 and uptake glucose, and adipocyte, skeletal muscle cell, hepatocyte and the like can be mentioned. These cells may be induced to differentiate from progenitor cells by a method known per se. For example, adipocyte may be induced to differentiate from 3T3L1 fibroblast.

As used herein, the "processing" means contacting the above-mentioned cell with DOPE for a time necessary and sufficient. While the time varies depending on the desired effect and the kind of the cells to be used, it is generally 0.1-3 hr, preferably about 0.2-2 hr. Conveniently, it is performed by cultivation in a culture medium containing DOPE.

The medicine of the present invention is generally given for the prophylaxis and/or treatment of diabetes, or for the prophylaxis and/or treatment of metabolic syndrome, while it varies depending on the age and condition of individual patients to be treated. In the case of intravenous administration, the daily dose of DOPE is 0.001-100 mg per 1 kg body weight of human or animal; in the case of intramuscular administration, the daily dose of DOPE is 0.001-10 mg per 1 kg body weight of human or animal; and in the case of oral administration, the daily dose of DOPE is 0.01-100 mg per 1 kg body weight of human or animal.

The medicine of the present invention can contain, besides DOPE which is the active ingredient, any additive, for example, a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatic substances such as citric acid, menthol, glycyllysin-ammonium salt, glycine, orange powder and the like, preservatives such as sodium benzoate, sodium bisulfite, methylparaben, propylparaben and the like, stabilizers such as citric acid, sodium citrate, acetic acid and the like, suspending agents such as methylcellulose, polyvinylpyrrolidone, aluminum stearate and the like, dispersing agents such as surfactant and the like, diluents to such as water, saline, orange juice and the like, base waxes such as cacao butter, polyethylene glycol, kerosene and the like, and the like.

In one embodiment, the medicine of the present invention can be formulated as a preparation preferable for oral administration. Examples of the preparation preferable for oral administration include a liquid wherein an effective amount of a substance is dissolved in a diluent such as water and saline, a capsule, granule, powder or tablet containing an effective amount of a substance as a solid or granules, a suspension wherein an effective amount of a substance is suspended in a suitable dispersion medium, an emulsion wherein a solution of an effective amount of a substance is dispersed and emulsified in a suitable dispersion medium, and the like.

In another embodiment, the medicine of the present invention can be formulated as a preparation preferable for parenteral administration. Examples of the preparation preferable for parenteral administration (e.g., intravenous injection, subcutaneous injection, muscular injection, topical injection and the like) include aqueous and nonaqueous isotonic aseptic injection liquids, which may contain antioxidant, buffer, bacteriostatic, isotonicity agent and the like. In addition, examples thereof include aqueous and non-aqueous aseptic suspensions, which may contain suspension, solubilizer, thickener, stabilizer, preservative and the like. Unit dose or plural doses of the preparation can be filled in a container such as ampoule and vial. Moreover, the active ingredient and a pharmaceutically acceptable carrier can be freeze-dried and preserved in a form that can be dissolved or suspended in a suitable aseptic vehicle immediately before use.

DOPE can be provided as food. DOPE as an active ingredient has, as mentioned above, (1) PKCα activation suppressive action, (2) suppressive action on GLUT4 endocytosis, and (3) blood glucose level-lowering action in mammal (e.g., mouse, rat, hamster, rabbit, cat, dog, bovine, sheep, monkey, human and the like), and can be provided as a functional food effective for the prophylaxis or treatment of diabetes or for the prophylaxis or treatment of metabolic syndrome.

The "food" in the present invention means all foods and drinks other than pharmaceutical products and quasi-drugs. For example, it includes, but is not limited to, food for specified health uses, food with nutrient function claims, and what is called supplements.

The medicine or food of the present invention may be packed or filled individually by a unit ingestion amount or a divided amount of the medicine or food, or packed or filled comprehensively by many unit ingestion amounts or divided amounts thereof.

When the medicine or food of the present invention is provided as a single preparation or food, the unit ingestion amount of the medicine or food or a divided amount thereof is the unit ingestion amount of DOPE or a divided amount thereof.

Examples of the medicine or food wherein a unit ingestion amount or a divided amount thereof is packed or filled individually include general packages (e.g., PTP (press through packing) sheet, paper container, film (e.g., plastic film) container, glass container, plastic container) packed or filled with the unit ingestion amount or a divided amount thereof. The medicine or foods that are individually packed or filled may be further combined and packed or filled in a single container (e.g., paper container, film (e.g., plastic film) container, glass container, plastic container). Examples of the medicine or food wherein many unit ingestion amounts or a divided amount thereof are/is comprehensively packed or filled include those wherein many tablets or capsules are packed or filled in a single container (e.g., paper container, film (e.g., plastic film) container, glass container, plastic container) without distinction. The medicine or food of the present invention may contain a unit ingestion amount or a divided amount thereof in a number sufficient for long-term ingestion. For example, a food can contain same in a number sufficient for ingestion for not less than 3 days, preferably not less than 7 days, 10 days, 14 days or 21 days, or 1 month, 2 months, or not less than 3 months.

Furthermore, DOPE has, as mentioned above, (1) PKCα activation suppressive action, (2) suppressive action on GLUT4 endocytosis, and (3) blood glucose level-lowering action, and therefore, can also be provided as various reagents. As the reagents, PKCα activity inhibitor, GLUT4 endocytosis inhibitor and the like can be specifically mentioned. The reagents can be a useful tool for developing a prophylactic and/or therapeutic drug for diabetes and metabolic syndrome, which has a conventionally-absent new action mechanism, shows reduced side effects and/or more enhanced effects.

While the present invention is explained in further detail in the following by referring to Examples, it is not limited by the following Examples and the like.

The contents disclosed in any publication cited in the present specification, including patents and patent applications, are hereby incorporated in their entireties by reference, to the extent that they have been disclosed herein.

EXAMPLE

Example 1

Verification of GLUT4 Endocytosis Suppressive Action of DOPE (Material and Method)

1. Cell Culture

3T3L1-GLUT4myc fibroblast strain expressing GLUT4myc was used. The cells are constructed by inserting human c-MYC epitope (14 amino acids) into the first ectodomain. The cells were cultured in Dulbecco's Modified Eagles Medium (DMEM) added with 10% (v/v) bovine serum, penicillin (final concentration, 100 U/ml) and streptomycin (final concentration, 0.1 mg/ml) in a humid environment under 5% $CO_2$ and 95% air at 37° C. When the cells reached confluence (day 0), the medium was exchanged with DMEM added with 10% (v/v) fetal bovine serum (FBS), 1 μM dexamethasone, 0.5 mM 3-isobutyl-methylxanthine and 0.1 mg/ml insulin to allow for differentiation from fibroblast into adipocyte. The medium was exchanged with DMEM added with 10% (v/v) FBS on day 3, day 7 and day 11. On day 14, the cell differentiated into adipocyte were used for the experiment.

2. GLUT4 Mobilization Monitoring

3T3L1-GLUT4myc adipocytes were incubated in Krebs-Ringer-HEPES buffer [136 mM NaCl, 4.7 mM KCl, 1.25 mM $CaCl_2$, 1.25 mM $MgSO_4$ and 20 mM HEPES, pH 7.5] containing 0.2% (w/v) BSA and added with 10 mM glucose at 37° C. for 1 hr. Then, the cells were homogenized by sonication in an ice-cooled mitochondria buffer [210 mM mannitol, 70 mM sucrose, and 1 mM ethylenediaminetetraacetic acid (EDTA), 10 mM HEPES, pH 7.5] containing 1% (v/v) protease inhibitor cocktail. Sequentially, the homogenate was centrifuged at 4° C. for 5 min at 3,000 rpm. The supernatant was further centrifuged at 4° C. for 15 min at 11,000 rpm. The recovered supernatant was ultracentrifuged at 4° C. for 60 min at 100,000 g, and separated into a cytoplasm fraction and a cellular membrane fraction. The supernatant was used as the cytoplasm fraction and the pellet was used as the cellular membrane fraction. Whether the cytoplasm component and the cellular membrane component could be successfully separated was confirmed by Western blot analysis using an antibody to LDH which is a cytoplasm component marker, and an antibody to cadherin which is a cellular membrane marker.

The protein concentration of each fraction was measured using BCA protein assay kit (Thermo Fisher Scientific, Waltham, Mass., USA). The protein of the cellular membrane fraction was resuspended in a mitochondria buffer containing 1% (w/v) sodium dodecyl sulfate (SDS). The protein of each fraction was separated by SDS-polyacrylamide gel electrophoresis (SDS-PAGE), and transferred onto polyvinylidene difluoride membranes. The blotting membranes were blocked with TBS-T [150 mM NaCl, 0.1% (v/v) Tween20 and 20 mM Tris, pH 7.5] containing 5% (w/v) BSA, reacted with anti-c-myc antibody (Merck Millipore, Darmstadt, Germany), and thereafter reacted with horseradish peroxidase (HRP) conjugate goat anti-mouse IgG antibody. The immunoreactivity was detected using ECL kit (Invitrogen), and visualized using a chemical luminescence detection system (chemiluminescence detection system; GE Healthcare, Piscataway, N.J., USA). The signal density was measured using an image analysis software (Image Gauge software; GE Healthcare).

3. Construction and Transfection of siRNA (Small Interfering RNA)

Akt1/2 siRNA was purchased from Santa Cruz Biotechnology, Inc. (Santa Cruz, Calif., USA). PKCα siRNA (PKCα KD) and siRNA (NC) as a negative control were purchased from Ambion (Carlsbad, Calif., USA).

As the sequence of siRNA for PKCα, 5'-GAACGUG-CAUGAGGUGAAAtt-3' (SEQ ID NO: 1) and 5'-UUU-CACCUCAUGCACGUUCtt-3' (SEQ ID NO: 2) were used.

As NC siRNA, a scrambled sequence having the same GC content and nucleic acid composition was used.

For transfection of each siRNA into the cell, Lipofectamine reagent (Invitrogen) was used. The cells at 48 hr after transfection were used for the experiment.

4. Western Blotting

3T3L1-GLUT4myc adipocytes were incubated in Krebs-Ringer-HEPES buffer [136 mM NaCl, 4.7 mM KCl, 1.25 mM $CaCl_2$, 1.25 mM $MgSO_4$ and 20 mM HEPES, pH 7.5] containing 0.2% (w/v) bovine serum albumin and added with 10 mM glucose at 37° C. for 1 hr. The cells were incubated in the presence or absence of various phosphoethanolamines for 10 min. Then, the cells were lysed in a lysis buffer [150 mM NaCl, 20 mM ethylenediaminetetraacetic acid, 0.5% (v/v) Nonidet P-40 and 50 mM Tris, pH 7.4] added with 1%(v/v) protease inhibitor cocktail at 4° C. for 5 min and centrifuged at 3,000 rpm. The supernatant was used as a total cell lysate.

For Western blotting, the protein was separated by SDS-polyacrylamide gel electrophoresis (SDS-PAGE) and transferred on a polyvinylidene difluoride membrane. The blotting membrane was blocked with TBS-T [150 mM NaCl, 0.1% (v/v) Tween20 and 20 mM Tris, pH 7.5] containing 5%(w/v) BSA, and successively reacted with phospho-Thr308-Akt1/2 [pT308], phospho-Ser-Aktl/2 [pS473], an antibody to Akt1/2 (Cell Signaling Technology, Inc., Danvers, Mass., USA), or an antibody against β-actin (Sigma, St. Louis, Mo., USA). After washing, the membrane was reacted with horseradish peroxidase (HRP) conjugate goat anti-rabbit IgG antibody. The immune reactivity was detected using ECL kit. (GE Healthcare, Piscataway, N.J., USA), and visualized using chemical luminescence detection system (chemiluminescence detection system; GE Healthcare). The protein concentration of each sample was measured using BCA protein assay kit (Thermo Fisher Scientific, Waltham, Mass., USA).

5. GLUT4 Internal Transfer (Uptake) Assay

3T3L1-GLUT4myc adipocytes were incubated in Krebs-Ringer HEPES buffer containing 0.2% (w/v) BSA and added with 10 mM glucose at 37° C. for 3 hr, and the cells were incubated with 100 nM insulin at 37° C. for 30 min. The cells were washed 3 times with ice-cooled Krebs-Ringer-HEPES buffer, and cultured in Krebs-Ringer-HEPES buffer warmed in advance and in the presence or absence of DOPE at 37° C. for 120 min.

(Results)

The cells not processed (Control) or processed with various phospholipid derivatives were dissolved and separated into cytoplasm (C) fraction and cellular membrane (M) fraction, and then Western blotting was performed using an anti-c-myc antibody. The results are shown in FIG. 1. The distribution of GLUT4 in cellular membrane was significantly increased only when processed with DOPE. The results show that DOPE has an action to increase cellular membrane distribution of GLUT4, and other phospholipid derivatives do not have such action.

Figure 2:
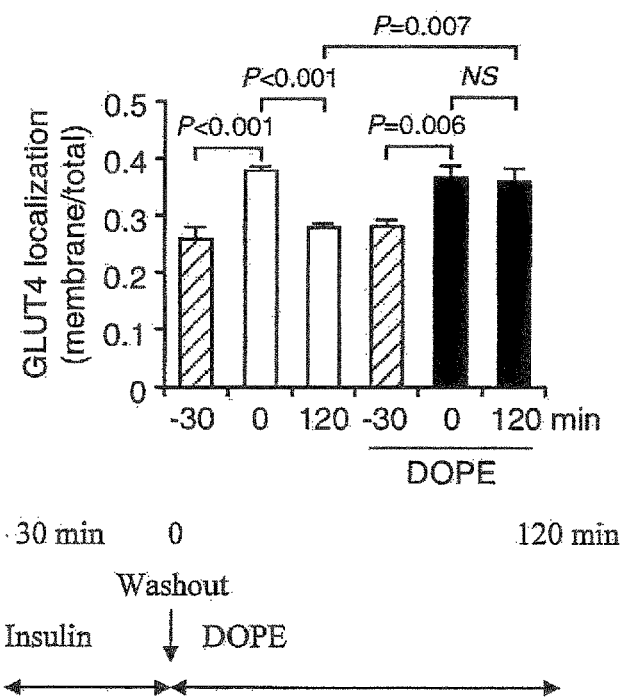
FIG. 2 is a graph showing that the GLUT4 cellular membrane distribution increasing action of DOPE derives from the suppression of GLUT4 endocytosis. 3T3L1-GLUT4myc adipocytes were treated with insulin (100 nM) for 30 min (−30-0 min), then washed to remove insulin (0 min), and DOPE (10 mM) was added to an extracellular solution. After incubation for 120 min, the cells were lysed, and separated into the cytoplasm (C) fraction and cellular membrane (M) fraction, after which Western blotting was performed using an anti-c-myc antibody. In the graph, each column shows mean (±SD) of the ratio: (signal intensity of c-myc in cellular membrane fraction)/(signal intensity of c-myc in in total cells) (n=4 in each experiment). P value, ANOVA (Bonferroni adjustment). NS; not significant.

The cells after pre-treatment with insulin (removed by washing) were treated (or untreated) with DOPE. The cells were dissolved, separated into cytoplasm (C) fraction and cellular membrane (M) fraction, and then Western blotting was performed using an anti-c-myc antibody. The results are shown in FIG. 2. In the absence of DOPE, GLUT4 was transported onto the cellular membrane by insulin stimulation; however, 120 min later, it was intracellularly uptaken by endocytosis. In contrast, in the presence of DOPE, endocytosis of GLUT4 transported onto the cellular membrane by insulin stimulation was suppressed.

Figure 3:
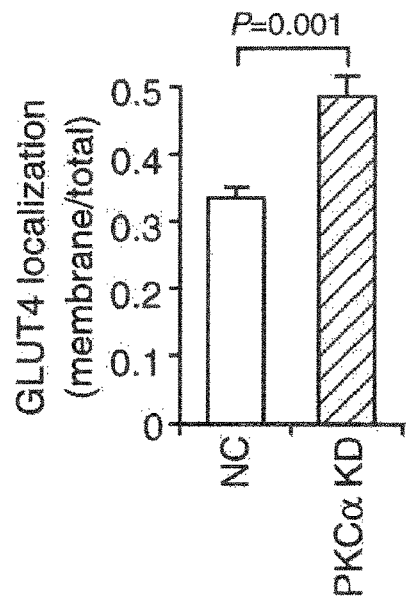
FIG. 3 is a graph showing that GLUT4 cellular membrane distribution increases by knocking down PKCα. 3T3L1-GLUT4myc adipocytes transfected with negative control NC siRNA (NC) or PKCα siRNA (PKCα KD) were lysed, and separated into the cytoplasm (C) fraction and cellular membrane (M) fraction, after which Western blotting was performed using an anti-c-myc antibody. In the graph, each column shows mean (±SD) of the ratio: (signal intensity of c-myc in cellular membrane fraction)/(signal intensity of c-myc in in total cells) (n=4 in each experiment). P value, unpaired t-test.

The 3T3L1-GLUT4myc adipocyte transfected with NC siRNA (NC) which is a negative control or PKCα siRNA (PKCα KD) was dissolved, separated into cytoplasm (C) fraction and cellular membrane (M) fraction, and then Western blotting was performed using an anti-c-myc antibody. The results are shown in FIG. 3. GLUT4 distribution on the cellular membrane significantly increased in the cells transfected with PKCα siRNA. The results show that PKCα knock down increases GLUT4 distribution on the cellular membrane. In other words, the results suggest that PKCα decreases GLUT4 distribution on the cellular membrane.

Figure 4:
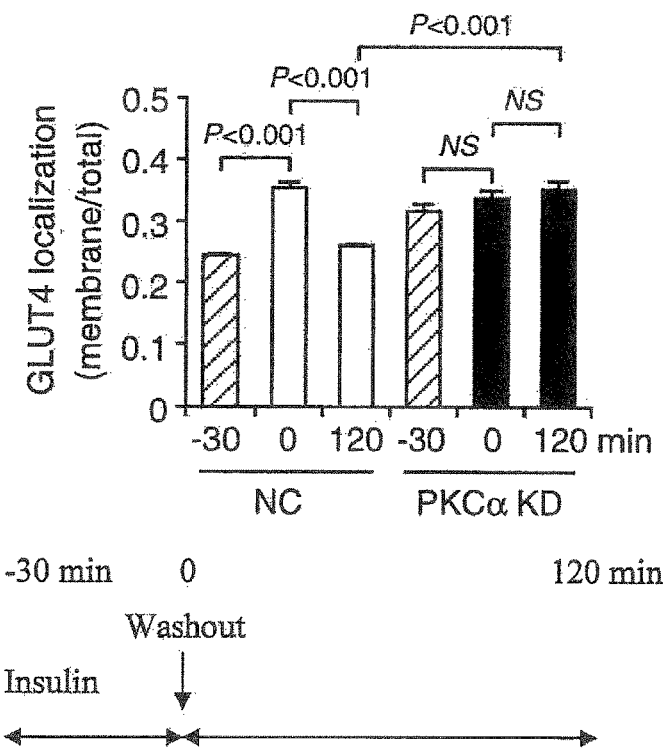
FIG. 4 is a graph showing that GLUT4 endocytosis is suppressed by knocking down PKCα, and GLUT4 cellular membrane distribution increases. 3T3L1-GLUT4myc adipocytes transfected with negative control NC siRNA (NC) or PKCα siRNA (PKCα KD) were treated with insulin (100 nM) for 30 min (−30-0 min), then washed to remove insulin (0 min). After incubation for 120 min, the cells were lysed, and separated into the cytoplasm (C) fraction and cellular membrane (M) fraction, after which Western blotting was performed using an anti-c-myc antibody. In the graph, each column shows mean (±SD) of the ratio: (signal intensity of c-myc in cellular membrane fraction)/(signal intensity of c-myc in in total cells) (n=4 in each experiment). P value, ANOVA (Bonferroni adjustment). NS; not significant.

Using 3T3L1-GLUT4myc adipocyte transfected with siRNA (NC) which is negative control NC or PKCα siRNA (PKCα KD), the cells after pre-treatment with insulin (removed by washing) were processed (or unprocessed) with DOPE, dissolved, separated into cytoplasm (C) fraction and cellular membrane (M) fraction, and then Western blotting was performed using an anti-c-myc antibody. The results are shown in FIG. 4.

GLUT4 is transported onto the cellular membrane by insulin stimulation, after which intracellularly uptaken by endocytosis, and GLUT4 on the cellular membrane decreases. However, the decrease was suppressed in the cells transfected with PKCα siRNA. The results show that endocytosis of GLUT4 transported onto the cellular membrane by insulin stimulation is suppressed by PKCα knock down. In other words, they suggest that PKCα stimulates GLUT4 endocytosis.

Example 2

Verification of PKCα Activation Suppressive Action of DOPE (Material and Method)
Cell Free PKC Assay PKC activity in a cell-free system was quantified by the methods described in previous reports (Kanno T et al. J Lipid Res 2006; 47:1146-1156). In short, synthesized PKC substrate peptide (10 μM) was reacted with various PKC isozymes in a medium containing 20 mM Tris-HCl (pH 7.5), 5 mM magnesium acetate, 10 μM ATP, in the presence or absence of DOPE (100 μm), in the presence or absence of 1 μM TPA (12-O-tetradecanoylphorbol-13-acetate) at 30° C. for 5 min. $Ca^{2+}$-free medium was used for novel PKC such as PKC-δ, -ε and the like, and a medium containing 100 μM $CaCl_2$ was used for other PKC isozymes. They were applied on reversed-phase HPLC (LC-10ATvp, Shimadzu Co., Kyoto, Japan), and the peak of substrate peptide and the peak of a new resultant product were measured by the absorbance at 214 nm. The areas of unphosphorylated PKC substrate peptide and phosphorylated PKC substrate peptide were measured (total area corresponds to the concentration of PKC substrate peptide used in this Example), and the amount of the phosphorylated substrate peptide was calculated. The amount (pmol/for 1 min) of substrate peptide phosphorylated per 1 min was used as an index of PKC activity.

(Results)

Figure 5:
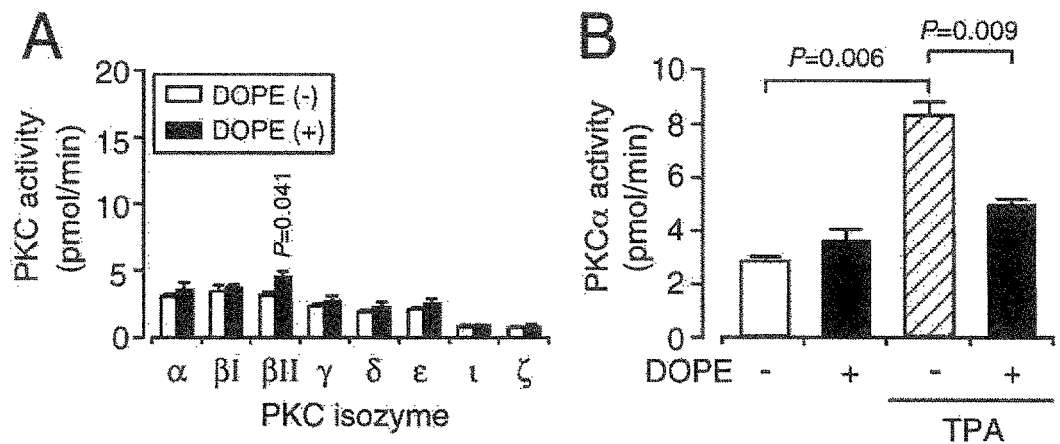
FIG. 5 is a graph showing that DOPE itself is not involved in PKC activation but has an action to suppress PKCα activated by TPA. PKC activity was monitored in a cell-free system. (A) Given PKC isozyme was evaluated in the absence or presence of DOPE (100 μM). In the graph, each column shows mean (±SEM) of PKC activity (pmol/min) (n=4). P value, compared to each PKC isozyme activation in the absence of DOPE, Dunnett's test. (B) The activity of PKCα was evaluated in the absence (control) or presence of DOPE (100 μM), in the absence or presence of TPA (1 μM). In the graph, each column shows mean (±SEM) of PKCα activity (pmol/min) (n=4). P value, Dunnett's test. TPA; 12-O-tetradecanoylphorbol-β-acetate.

The results are shown in FIG. 5. The results show that DOPE is not involved in PKC activation, but has an action to suppress PKCα activated by TPA.

Example 3

Verification of Blood Glucose Level-lowering Action of DOPE (Material and Method)
Glucose Tolerance Test C57BL/KsJ-lepr$^{db}$/lepr$^{db}$ mouse (female, 8-week-old) (CLEA Japan; Tokyo, Japan) was used. Glucose tolerance test was performed using the mouse starved for 12 hr. Glucose (2 g/ml/kg body weight) was administered by gavage, and the time point thereof was taken as 0 h. DOPE (0, 0.1, 1, 10 mg/kg) was orally administered 30 min before administration of glucose. Brine was used for DOPE (0 mg/kg). The blood (10 μl) was collected from the tail vein at the time points of 30, 60, and 90 min, and each plasma sample which was labeled with 4-aminobenzyl ethyl ester (ABEE) and prepared from the obtained blood was loaded on high performance liquid chromatography (HPLC) system (LC-10ATvp; Shimadzu Co., Kyoto, Japan). The glucose concentration was calculated from a peak area/concentration analytical curve prepared using the standard glucose solution.

(Results)

Figure 6:
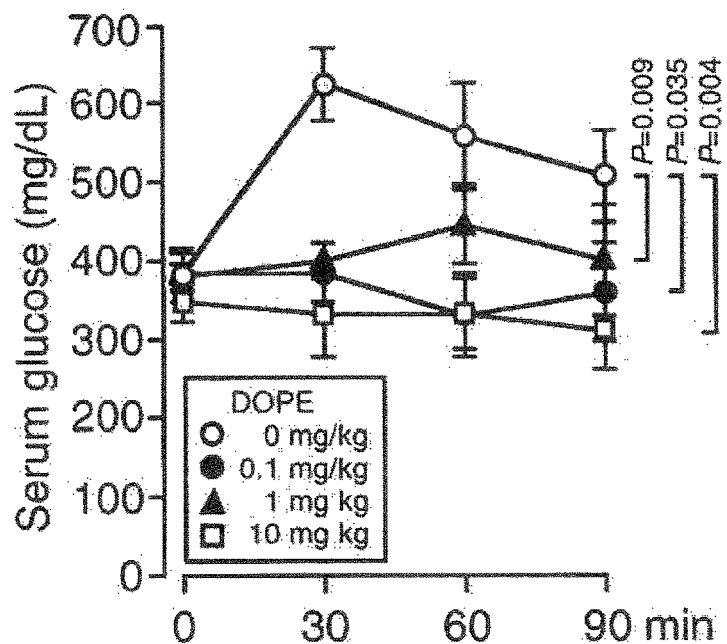
FIG. 6 is a graph showing that DOPE decreases the serum glucose level in C57BL/KsJ-lepr$^{db}$/lepr$^{db}$ mouse. The mouse was placed in glucose starvation for 12 hr, glucose (2 g/kg) was orally administered, the blood was recovered at a given time and serum glucose assay was performed. DOPE was orally administered at a given concentration (0-10 mg/kg) 30 min before administration of glucose. In the graph, each point shows mean (±SEM) of serum glucose concentration (n=5 in each experiment). P value, Fisher's PLSD (Protected Least Significant Difference test).

The results are shown in FIG. 6. The results show that DOPE has an action to decrease blood glucose level of type 2 diabetes model mouse in a dose dependent manner.

From the above results, usefulness of DOPE in the treatment of diabetes and metabolic syndrome, namely, suppression of PKCα activation→suppression of intracellular transport (endocytosis) of GLUT4→increase of GLUT4 distribution on cellular membrane→increase of sugar uptake from outside to inside of the cell→application to diabetes treatment, has been clarified.

[Sequence Listing Free Text]
SEQ ID NO: 1: siRNA
SEQ ID NO: 2: siRNA

INDUSTRIAL APPLICABILITY

DOPE has a pharmacological action superior for the treatment of diabetes (protein kinase Cα (PKCα) activation suppressive action, suppressive action on glucose transporter 4 (GLUT4) endocytosis and blood glucose level-lowering action), and therefore, is useful as a therapeutic drug for diabetes. It is also useful as various reagents based on such pharmacological action.

This application is based on patent application No. 2014-007232 filed in Japan (filing date: Jan. 17, 2014), the contents of which are encompassed in full herein.

The invention claimed is:

1. A method of suppressing GLUT4 endocytosis, comprising contacting a cell that expresses GLUT4 and is capable of glucose uptake with a composition consisting of 1,2-dioleoyl-sn-glycero-3-phosphoethanolamine (DOPE), thereby suppressing GLUT4endocytosis in the cell.

2. The method according to claim 1, wherein suppression of GLUT4 endocytosis is caused by suppressing PKCα activation.

3. The method of claim 1, wherein the cell is an adipocyte.

4. The method of claim 1, wherein the cell is a skeletal muscle cell.

5. The method of claim 2, wherein the cell is an adipocyte.

6. The method of claim 2, wherein the cell is a skeletal muscle cell.

* * * * *